United States Patent
Seering et al.

(10) Patent No.: US 6,783,506 B2
(45) Date of Patent: Aug. 31, 2004

(54) TROCHANTER BELT

(76) Inventors: Christine L. Seering, 6659 Poplar, P.O. Box 443, Hamburg, MI (US) 48139; Mona E. Seering, 1818 Blue Gill Ave., Clare, MI (US) 48617

( * ) Notice: Subject to any disclaimer, the term of this patent is extended or adjusted under 35 U.S.C. 154(b) by 0 days.

(21) Appl. No.: 10/237,340

(22) Filed: Sep. 9, 2002

(65) Prior Publication Data

US 2004/0049142 A1 Mar. 11, 2004

(51) Int. Cl.$^7$ .................................................. A61F 5/00
(52) U.S. Cl. .......................................... 602/19; 128/876
(58) Field of Search .............. 602/5, 19; 128/869–876; 450/155; 2/44, 311–314, 317–319

(56) References Cited

U.S. PATENT DOCUMENTS

| | | | |
|---|---|---|---|
| 4,696,291 A | | 9/1987 | Tyo |
| 4,715,364 A | | 12/1987 | Noguchi |
| 4,794,916 A | * | 1/1989 | Porterfield et al. ............ 602/19 |
| 5,232,424 A | * | 8/1993 | Pearson et al. ............. 482/106 |
| 5,259,831 A | * | 11/1993 | LeBron ......................... 602/7 |
| 5,295,947 A | * | 3/1994 | Muncy ........................... 602/5 |
| 5,363,863 A | * | 11/1994 | Lelli et al. ................... 128/876 |
| 5,407,422 A | | 4/1995 | Matthijs et al. |
| 5,433,697 A | * | 7/1995 | Cox .............................. 602/19 |
| 5,647,378 A | * | 7/1997 | Farnum ....................... 128/876 |
| 5,690,609 A | * | 11/1997 | Heinze, III .................. 602/19 |
| 5,722,940 A | * | 3/1998 | Gaylord et al. ............... 602/19 |
| 5,785,671 A | * | 7/1998 | Striano ........................ 602/19 |
| 5,926,853 A | | 7/1999 | Plank |
| 6,099,490 A | * | 8/2000 | Turtzo .......................... 602/19 |
| 6,352,074 B1 | | 3/2002 | Okada |
| 6,427,697 B1 | * | 8/2002 | Pearcey ....................... 128/876 |
| 2002/0082537 A1 | * | 6/2002 | MacAllister ................... 602/4 |
| 2002/0087105 A1 | * | 7/2002 | Grosso ......................... 602/13 |

* cited by examiner

Primary Examiner—Nicholas D. Lucchesi
Assistant Examiner—Huong Q. Pham
(74) Attorney, Agent, or Firm—Brooks Kushman P.C.

(57) ABSTRACT

A trochanter belt with an elastic front portion 10 comprised of a soft inner surface which conforms to the body of the wearer. Right and left elastic side portions 12 connect to the right and left sides of the inelastic front portion 10. The right and left elastic portions 12 also connect to the right and left side of the inelastic back portion 14 to create a continuous band of support which does not require disassembly to remove. Right and left adjustable straps 16 are attached to the continuous belt on the right and left sides, respectively.

8 Claims, 3 Drawing Sheets

TROCHANTER BELT

BACKGROUND OF THE INVENTION

1. Field of the Invention

This invention relates to a trochanter belt for stabilizing the hips and pelvis by providing firm support around the hips.

2. Background Art

Illustrative of the prior art is U.S. Pat. No. 5,690,609 which issued to Frank D. Heinze, III on Nov. 25, 1997 That reference discloses a compound abdominal and back support belt system. However, the garment disclosed by that reference is a bulky and cumbersome system which is threaded in a complex fashion and requires disassembly to be removed from the body. Accordingly, there remain unsolved problems associated with difficulties in use and comfort.

SUMMARY OF THE INVENTION

The present invention presents a belt which is light weight, simple, and easy to use.

It is a principal object of the present invention to provide targeted support to appropriate areas by pressure exerted on an adjustable material that includes elastic portions and relatively inelastic portions, the length of which can be adjusted.

It is another object of the invention to provide a simple system which can be easily used and is not bulky or cumbersome.

In carrying out the above objects and other objects and features, a continuous band of material is provided that has two portions of an adjustable material and two portions of non-adjustable material.

The invention has an inelastic front portion consisting of an inner surface and an outer surface. The outer surface is adapted to mate with a Velcro®-like surface. The inelastic front portion is continuous with an elastic side portion on both the right and left sides. A rear inelastic portion is connected to and joins the two elastic side portions. This creates a continuous circle which does not require disassembly but can be easily slid onto and off of the body. This design provides a continuous system of support and a light weight design.

More particularly, attached to the front and rear portions are adjustable bands which allow easy modification of the amount of compression. The adjustment straps are on both the right and left sides and are composed of a fixed end and an adjustable end. The adjustable end can be detachably attached to itself or to the rear inelastic portion. The fixed end is attached to the front inelastic member or fixed end. The elastic side portions when compressed using the adjusting bands apply targeted support to the right and left areas.

Further, the adjustable bands are capable of being attached by various means for attachment such as: Velcro®, press studs, buckles, buttons, detachable belt assemblies, snap-fitted devices or hooks and eyes and their equivalents. The adjustment bands and adjustable side portions create a readily conforming belt which is flexible and soft against the body. The adjustable bands are made of a soft material and consist of two-way threading that does not require a change in threading to allow removal of the device.

DETAILED DESCRIPTION OF THE PREFERRED EMBODIMENTS

Figure 1:
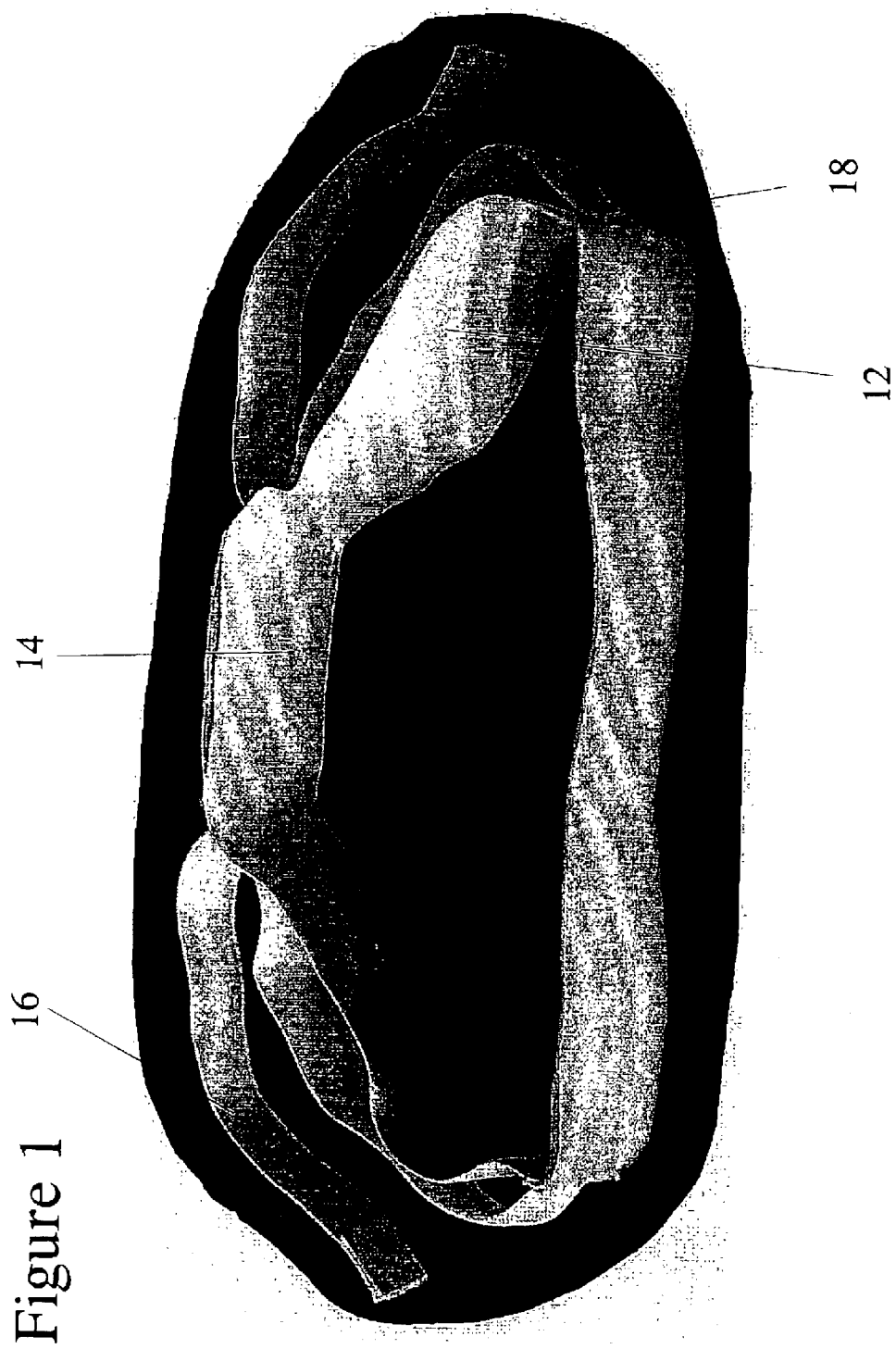
FIG. 1 is a front perspective view of the trochanter belt.
Figure 2:
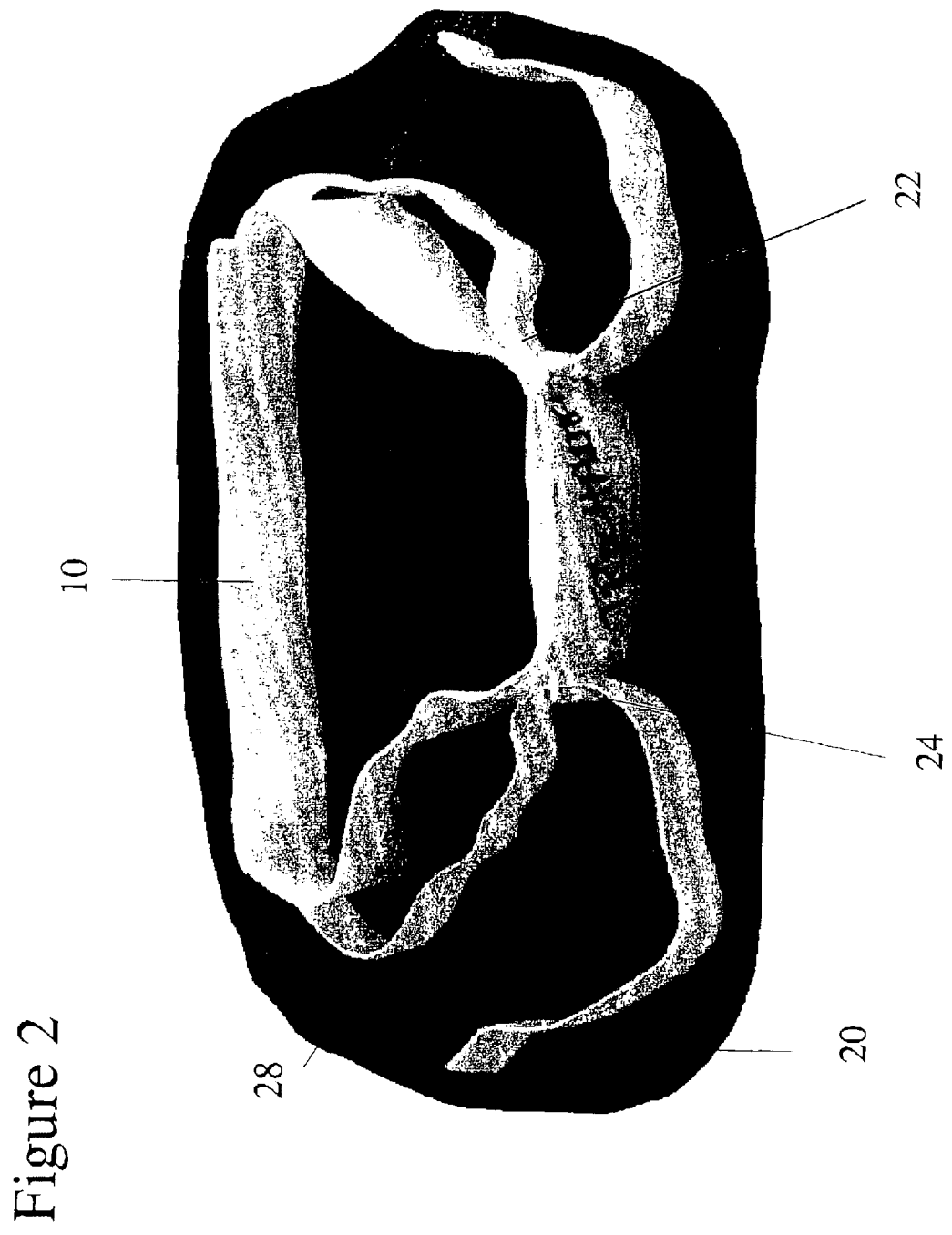
FIG. 2 is a back perspective view of the trochanter belt.

The trochanter belt is configured to provide a light weight, comfortable and easy to use support system for stabilization of the hips. The inside surface of the inelastic front portion 10 (FIGS. 1–2) is made of a soft material which conforms to the body of the wearer for comfort and support. Joined to the inelastic front portion 10 on the right and left sides respectively, are the right and left elastic sections 12. The right and left elastic side sections 12 are in turn attached to the right and left side, respectively, of the inelastic back portion 14 which creates a continuous band. The right and left elastic sections 12 allow the continuous band to be slipped onto and off of the body without disassembling any of the portions.

Attached to the right and left sides are adjustment bands 16, which provide structure and a method for controlling the amount of compression provided by the belt. A fixed end of the right and left adjustable straps 18 is attached to the right and left sides, respectively, of the inelastic front portion 10. The adjustable end 20 (FIG. 2) can be detachably attached to the front inelastic portion 10 or to an outer surface 28 of the adjustable strap to allow modification of compression of the belt. Although the terms "front" and "back" and "left" and "right" are used in this disclosure, it will be readily apparent that these terms can be used interchangeably. For example, a physician or the wearer may prefer to use the disclosed trochanter belt so that the inelastic portions are located on both hips. In that case, the "front" and "back" portions are positioned on the right or left side of the wearer, or, if desired, at positions that are intermediate therebetween.

Figure 3:
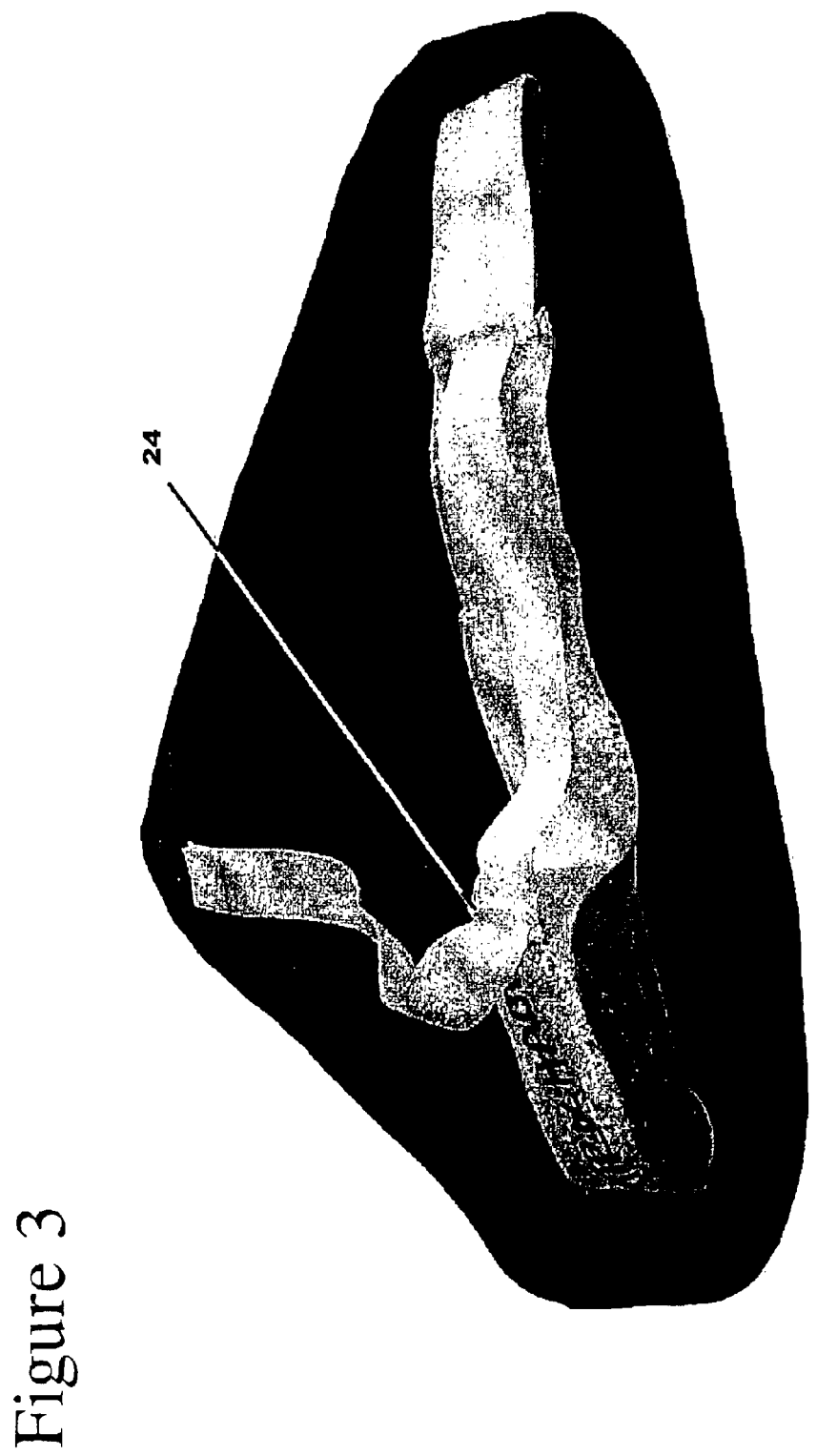
FIG. 3 is a left elevation side view of the trochanter belt.

Modification is achieved by pulling the adjustable intermediate portion 22 through the eyelet 24 (FIG. 3) and reattaching the adjustable end 20 to the front inelastic portion 10 or to an outer surface 28 of the adjustable strap. The eyelet 24 is in turn attached to the back portion 14.

If desired, hip pads may be used in place of the inelastic portion. In this embodiment, there is added utility in the case of elderly persons who may be unstable and prone to falling. Additionally, such pads could be applied to provide localized support and protection.

Preferably, the width of the trochanter belt is about 3 inches. However, such a width may not be suitable for all wearers. For example, if a person weighs 400 pounds, a band having a width of about 3 inches would not cover the area needed for support. In such cases, a width of about 6–12 inches would be more suitable. Additionally, if hip protectors are incorporated, then the width of the belt would be larger than 3 inches. Thus, it can be seen that the desired width is selected according to the intended application.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A trochanter belt comprising:

an inelastic front portion that exerts a continuous inward compression upon a wearer, the front portion containing a soft inner surface which conforms to the body of the wearer and an outer surface, the front portion having right and left sides and a width;

right and left elastic side portions having a width being approximately the same as the width of the inelastic front portion respectively extending from the right and left sides of the inelastic front portion;

an inelastic, comformable back portion of a width approximately equal to the width of the front and side portions;

the right and left elastic side portions also connecting to the right and left side of the inelastic back portion, the front portion and right and left side portions and the back portion creating over their width a continuous support which does not require disassembly to remove; and right and left straps that provide an adjustable length that are attached to the right and left sides of the inelastic front portion, respectively, the front, side and back portions being serially connected forming an unbroken loop before and during deployment and thereby cooperating to provide an uninterrupted, inwardly-directed pressure on the wearer.

2. A trochanter belt according to claim 1, wherein the right and left adjustable straps include a fixed end attached to the right and left sides of the inelastic front portion and an adjustable end that can be detachably attached proximate the front inelastic portion or to an outer surface of the adjustable strap.

3. A trochanter belt according to claim 1, wherein the right and left adjustable straps include an intermediate portion and a distal end, the right and left straps engaging an eyelet which is attached to the back portion, the distal end having an adhesive section that can be adjustably and detachably attached to the outer surface of the front portion or to the outer surface of the adjustable strap.

4. A trochanter belt according to claim 2, wherein the right and left adjustable straps are attachable by press studs, buttons, detachable belt assemblies, snap-fitted devices, or hooks and eyes.

5. A trochanter belt according to claim 1, wherein inward support provided by the right and left elastic side portions is localized and adjustable by altering the length of the adjustable straps and attaching a distal end thereof to control the amount of compression applied.

6. A trochanter belt according to claim 1, wherein the belt width does not exceed a width of 6–12 inches.

7. A trochanter belt according to claim 2, wherein the right and left adjustable straps include means for attachment of their adjustable ends proximate the front inelastic portion or to an outer surface of the adjustable strap.

8. A trochanter belt comprising:

an inelastic front portion that exerts a continuous inward compression upon a wearer, the front portion containing a soft inner surface which conforms to the body of the wearer and an outer surface, the front portion having right and left sides and a width;

right and left elastic side portions which respectively extend from the right and left sides across substantially the entire width of the inelastic front portion;

an inelastic, comformable back portion of a given width;

the right and left elastic side portions also connecting to the right and left side of the inelastic back portion across substantially its entire width, the front portion and right and left side portions and the back portion creating over their width a continuous support which does not require disassembly to remove; and right and left straps that provide an adjustable length that are attached to the right and left side of the inelastic front portion, respectively, the front, side and back portions being serially connected forming an unbroken loop before aid during deployment and thereby cooperating to provide an uninterrupted, inwardly-directed pressure on the wearer.

* * * * *

UNITED STATES PATENT AND TRADEMARK OFFICE
CERTIFICATE OF CORRECTION

PATENT NO. : 6,783,506 B2
DATED : August 31, 2004
INVENTOR(S) : Christine L. Seering et al.

It is certified that error appears in the above-identified patent and that said Letters Patent is hereby corrected as shown below:

Column 4,
Line 35, delete "aid" and insert -- and --.

Signed and Sealed this

Eighteenth Day of January, 2005

JON W. DUDAS
*Director of the United States Patent and Trademark Office*